United States Patent
Mastrorio

Patent Number: 6,152,930
Date of Patent: Nov. 28, 2000

[54] ACETABULAR CUP EXTRACTION SYSTEM

[75] Inventor: Brooke W. Mastrorio, Lakeville, Mass.

[73] Assignee: DePuy Orthopaedics, Inc., Warsaw, Ind.

[21] Appl. No.: 09/182,394

[22] Filed: Oct. 28, 1998

[51] Int. Cl.$^7$ .................................................. A61B 17/00
[52] U.S. Cl. ............................................... 606/99; 606/91
[58] Field of Search .................. 623/22; 606/53, 606/86, 91, 99

[56] References Cited

U.S. PATENT DOCUMENTS

| | | | |
|---|---|---|---|
| 3,859,992 | 1/1975 | Amstutz | 606/91 |
| 4,305,394 | 12/1981 | Bertuch, Jr. | 606/91 |
| 4,475,549 | 10/1984 | Oh | 128/303 R |
| 4,528,980 | 7/1985 | Kenna | 606/80 |
| 4,632,111 | 12/1986 | Roche | 606/53 |
| 4,716,894 | 1/1988 | Lazzeri et al. | 128/92 V |
| 4,936,863 | 6/1990 | Hofmann | 623/23 |
| 5,030,221 | 7/1991 | Buechel et al. | 606/91 |
| 5,112,338 | 5/1992 | Anspach, III | 606/99 |
| 5,250,051 | 10/1993 | Maryan | 606/91 |
| 5,320,625 | 6/1994 | Bertin | 606/91 |
| 5,352,230 | 10/1994 | Hood | 606/99 |
| 5,364,403 | 11/1994 | Petersen et al. | 606/91 |
| 5,370,704 | 12/1994 | DeCarlo, Jr. | 623/22 |
| 5,417,696 | 5/1995 | Kashuba et al. | 606/9.1 |
| 5,431,657 | 7/1995 | Rohr | 606/91 |
| 5,486,181 | 1/1996 | Cohen et al. | 606/91 |
| 5,569,262 | 10/1996 | Carney | 606/96 |
| 5,571,111 | 11/1996 | Aboczky | 606/91 |
| 5,571,200 | 11/1996 | Cohen et al. | 623/22 |
| 5,658,294 | 8/1997 | Sederholm | 606/91 |
| 5,683,399 | 11/1997 | Jones | 606/91 |
| 5,928,287 | 7/1999 | Keller | 623/22 |

FOREIGN PATENT DOCUMENTS 0535973   4/1991   European Pat. Off. .................. 606/91

*Primary Examiner*—Paul J. Hirsch
*Assistant Examiner*—Michael B. Priddy
*Attorney, Agent, or Firm*—Nutter, McClennen & Fish, LLP

[57] ABSTRACT

An acetabular cup extraction system includes a sealing member which is securable to an implanted acetabular cup. A elongate member is engagable with the sealing member to facilitate removal of the cup from the patient's acetabulum. In one embodiment, the sealing member includes a passage for coupling with a vacuum source to evacuate an interior portion of the cup and thereby enhance the engagement of the sealing member to the acetabular cup.

16 Claims, 5 Drawing Sheets

ACETABULAR CUP EXTRACTION SYSTEM

CROSS REFERENCE TO RELATED APPLICATION

Not Applicable.

STATEMENT REGARDING FEDERALLY SPONSORED RESEARCH

Not Applicable.

BACKGROUND OF THE INVENTION

The invention relates generally to systems for extracting prosthetic components, and more particularly, to systems for extracting an implanted acetabular cup from the acetabulum of a patient.

Joint arthroplasty is a well known surgical procedure by which a diseased and/or damaged natural joint is replaced by a prosthetic joint. Joint arthroplasty is commonly performed for hips, knees, elbows, and other joints. The health and condition of the joint to be replaced dictate the type of prosthesis necessary to replace the natural joint. For example, in a total hip arthroplasty an acetabular cup is implanted in the acetabular cavity in the pelvis to replace the natural acetabulum. Replacement of the acetabulum is necessary when there is an inadequate articulation surface for a head or ball of a prosthetic femoral component.

To implant an acetabular cup, a cavity is reamed in the acetabulum. The reamed cavity generally conforms to an outer surface of the acetabular cup. The acetabular cup is then inserted into the formed cavity and secured by mechanical means, by interference fit, or by a combination thereof. The acetabular cup is positioned in the pelvis at a fixed orientation in the acetabulum so as to emulate the patient's natural anatomy. The implanted cup should remain stable to prevent erosion of the surrounding bone and to inhibit generation of excessive wear debris in the prosthetic joint.

Various methods and techniques have been used to secure an acetabular cup within a formed acetabular cavity. One such method includes the use of bone cement to secure the acetabular cup to the acetabulum. Another technique utilizes an acetabular cup having holes for receiving screws, or other types of fasteners, to affix the acetabular cup to bone. A further method includes the implantation of an acetabular cup having an outer surface with various surface features to enhance fixation of the cup within the acetabular cavity.

While the above-described techniques achieve varying levels of success in providing long term fixation of the acetabular cup, surgical revision of the implanted cup is often necessary after an extended period of time. However, removal of the acetabular cup, especially cups without engagable inner surface features, can be difficult. In one technique for removing acetabular cups without inner surface features, such as an inner lip, osteotomes are taken about the outer surface of the acetabular cup and brute force is applied to achieve removal of the cup. More particularly, an osteotome chisel (see FIG. 7) is used to chisel away material at the cup/bone or bone/cement interface until the cup can be forcibly removed from the acetabulum. However, the aggressive use of force can result in the loss and/or fracture of essential bone. This difficult and awkward procedure poses a significant obstacle to successful surgical revision of an acetabular cup.

It would, therefore, be desirable to provide a system for removing implanted acetabular cups, and particularly cups without inner surface features, which minimizes the need for osteotomes, as well as the amount of force required to remove the implanted cup.

SUMMARY OF THE INVENTION

The present invention provides a system for removing an implanted prosthetic component. Although the invention is primarily described in conjunction with removing an implanted acetabular cup, it is understood that the system is applicable to a variety of implanted prosthetic joint components as well.

In one embodiment, a system for extracting an implanted acetabular cup includes a generally annular plug which is matable with a rim region of the cup. A recess is formed about a circumference of the plug so as to provide first and second disc-shaped portions. The first portion has a first diameter and the second portion has a second diameter which is less than the first diameter. The periphery of the first and second portions form a mating surface for engaging corresponding inner and outer rim regions of the acetabular cup. An elongate member or handle has a first end for coupling with the plug and a second end for manipulation by a user to facilitate removal of the cup.

The plug can include a passageway for coupling to a vacuum source. When the plug is seated within the rim of the cup so as to form a seal, the passageway provides fluid communication between a remote vacuum source and an interior region of the cup. A valve mechanism controls the opening and closing of the passageway. To enhance the mechanical engagement between the plug and the cup, the interior region of the cup can be evacuated to a predetermined pressure. The resulting vacuum increases the ability of the plug to resist displacement from the cup as pressure applied to a proximal end of the handle is communicated to the plug via the handle.

The secure engagement of the plug and the implanted cup allows a surgeon to manipulate the handle for gently rotating the implanted cup. By rotating the cup, the surgeon can expose underlying cement and/or bony ingrowth. A conventional osteotome can then be used to dislodge material disposed about the outer surface of the cup and ultimately free it from the acetabulum.

In another embodiment, the handle has a threaded distal end for engaging corresponding threads on the plug. The distal end is tapered such that radially outward pressure on the mating surface of the plug increases as the handle is rotated. The threaded distal end can form a seal with the plug so as allow evacuation of the interior region of the cup to further enhance mechanical engagement of the plug and the cup.

In a further embodiment, a chamber is formed in the plug for selectively urging the mating surface against the rim of the acetabular cup. In one embodiment, the plug is first mated with the cup and the chamber is filled with a pressurized fluid so as cause an expansion of the mating surface. In an alternative embodiment, the plug is evacuated after which the plug is seated within the cup rim. The vacuum is then released so as to cause the mating surface to expand and thereby engage the rim.

In yet another embodiment, the plug includes an expansion member housed therein. The expansion member is formed from a shape memory material which has a thermally dependent geometry. In one embodiment, the plug is seated within the cup rim and the expansion member is heated which changes the shape of the expansion member so as to urge the mating surface against the rim. Alternatively, the expansion member is first cooled so as to effect a contraction of the mating surface. The plug is then seated within the rim region of the cup and the expansion member is heated so as to force the mating surface against the rim.

BRIEF DESCRIPTION OF THE DRAWINGS

The invention will be more fully understood from the following detailed description taken in conjunction with the accompanying drawings, in which.

DETAILED DESCRIPTION OF THE INVENTION

Figure 1:
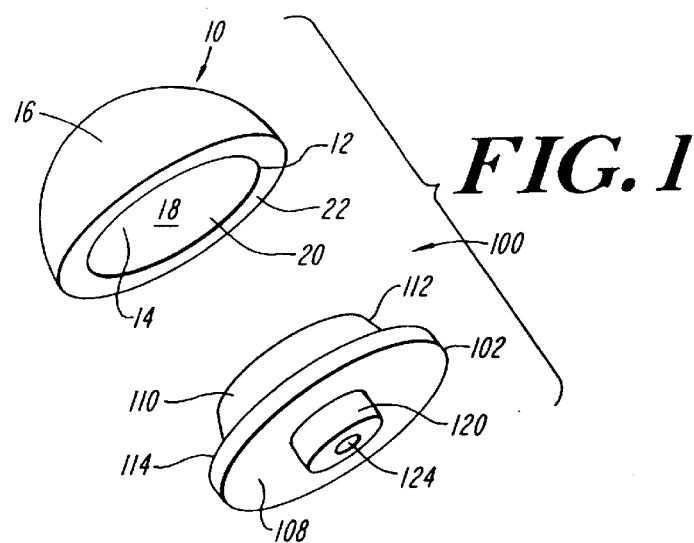
FIG. 1 is a perspective view of a part of a system for extracting an implanted acetabular cup in accordance with the present invention, shown at a first angle.
Figure 2:
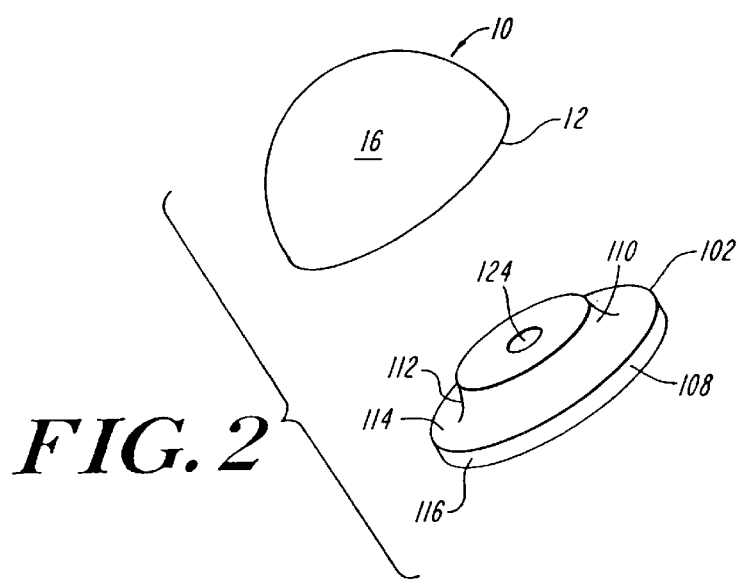
FIG. 2 is a perspective view of the system of FIG. 1, shown at a second angle.

FIGS. 1–2 show part of a system 100 for extracting an implanted acetabular cup 10 from the acetabular cavity of a patient. In general, a plug 102 is securable to a rim region 12 of the acetabular cup to enable the application of pressure to the implanted cup 10 for facilitating its removal from the patient's acetabulum. A handle 104 (FIG. 6) can be engaged with the plug 102 to provide a mechanism for accurately applying force to the acetabular cup 10. The cup extraction system 100 of the present invention is particularly useful for extracting acetabular cups which lack engagable surface features formed on an inner surface 14 of the cup.

The exemplary acetabular cup 10 shown in FIGS. 1–2 includes a convex outer surface 16 which is adapted for fixation to bone by means of interference engagement, cement and/or bony ingrowth. Typically, the acetabular cup 10 is inserted into a spherical cavity reamed in the patient's acetabulum. The formed cavity should provide adequate initial fixation of the acetabular cup within the patient's acetabulum and should enhance long term stability of the implant. However, after an extended period of time surgical revision of the implanted cup 10 may ultimately become necessary due to cup migration and/or loosening. In a surgical revision procedure, the originally implanted cup must be removed from the patient's acetabulum. It is important, however, that the cup 10 be extracted without removing essential bone and tissue. The plug 102 and handle 104 assembly (FIG. 6), which forms a part of the extraction system 100, allows cup extraction without the need for potentially destructive force levels being applied to the implanted cup. Further, the need for osteotomes to extract the cup is reduced or eliminated entirely.

The plug 102 can be formed in a variety of geometries adapted for optimal coupling with a range of acetabular cups. It is understood that the shape of the plug 102 can vary to accommodate an acetabular cup having particular inner and/or outer geometries, such as an oblong shape. In general, the plug 102 should be securely engagable with the acetabular cup 10. The plug 102 should also be matable with a handle 104 (FIG. 6) which communicates applied pressure to the acetabular cup.

Figure 3:
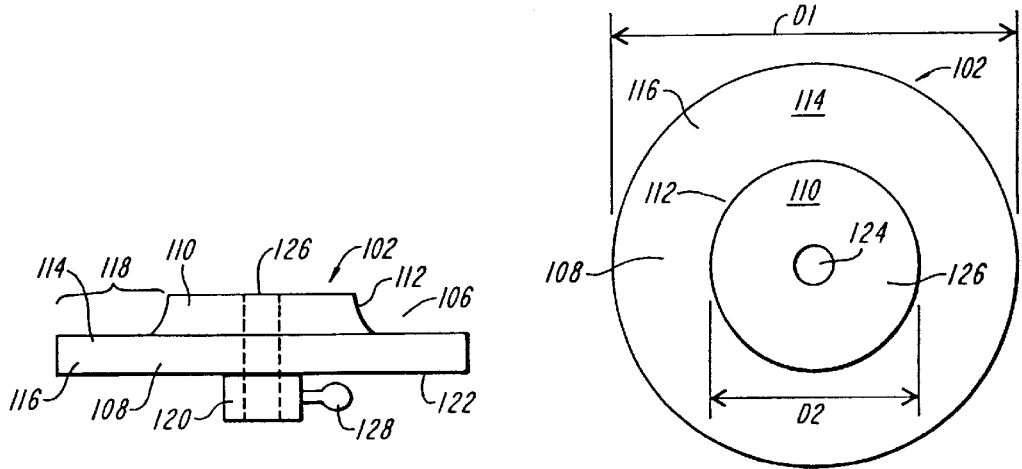
FIG. 3 is a side view of a plug which forms a part of the system of FIG. 1.
Figure 4:
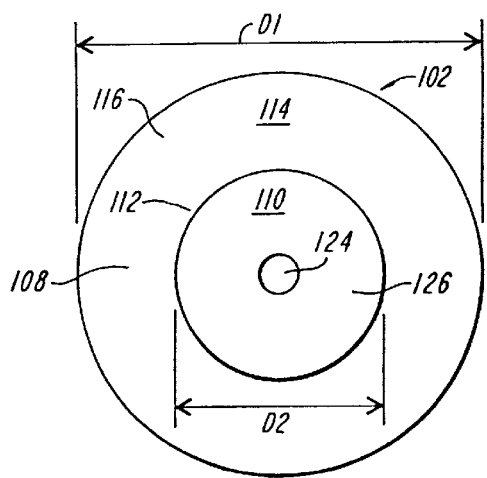
FIG. 4 is a top view of the plug of FIG. 3.

Referring now to FIGS. 3–4 in combination with FIG. 1–2, the plug 102 is generally annular with a recess 106 formed about a circumference of the plug so as to form a first disc-shaped portion 108 having a first diameter D1 and a second disc-shaped portion 110 having a second diameter D2, which is less the first diameter D1. The second portion 110 has an outer surface 112 for achieving mechanical engagement of the rim region 12 of the cup and the plug 102. In the illustrated embodiment, the outer surface 112 is shown as being tapered and slightly arcuate. However, it is understood that the outer surface 112 can be generally perpendicular to the first portion 110 or it can be tapered with or without curvature. Although not shown, it is further understood that the outer surface 112 can include a variety of surface features, such as steps, bumps and/or protrusions for enhancing engagement of the plug to the cup. The plug second portion 110 is adapted for insertion into an interior region 18 of the cup such that the outer surface 112 abuts an inner rim region 20 of cup. The plug first portion 108 has a shoulder 114 for abutting an outer rim region 22 of the cup and a lip 116. The outer surface 112 of the plug second portion 110 and the shoulder 114 of the first portion 108 form a mating surface 118 which generally complements the rim region 12 of the cup so as to seal the interior region 18 of the cup.

The plug 102 can have an optional collar 120 protruding from a bottom surface 122 of the plug. A passage 124 can extend through the collar 120 to a top surface 126 of the plug 102. Coupled to the collar 120 is a stopcock 128 for selectively opening and closing the passage 124.

Figure 5:
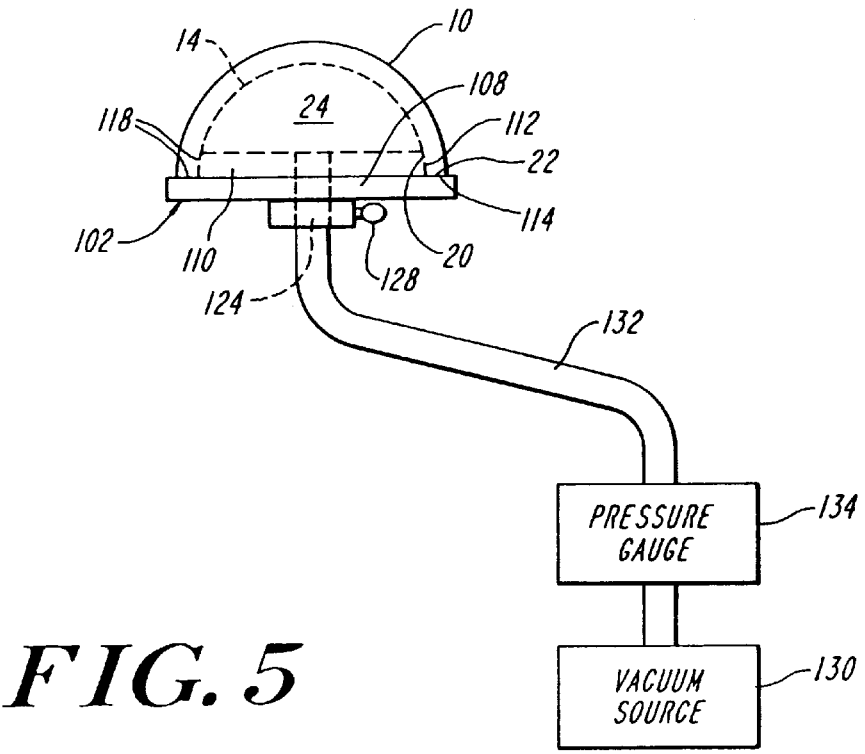
FIG. 5 is a block diagram showing the plug of FIG. 3 coupled to a vacuum source.

FIG. 5 shows the plug 102 mated with the acetabular cup 10 and coupled to a vacuum source 130 via a hose 132. A pressure gauge 134 can be connected to the hose 132 to enable vacuum pressure regulation. The passage 124 through the plug 102 provides fluid communication to an interior region 24 of the implanted cup 10. For an acetabular cup having screw holes or other openings, a fluid impermeable sheet member (not shown) can be bonded to the inner surface 14 of the cup so as to allow evacuation of the cup inner region.

In operation, the plug 102 is mated to the acetabular cup 10 such that the mating surface 118 of the plug engages the rim region 12 of the cup. That is, the outer surface 112 of the plug second portion 110 abuts the inner rim region 20 of the cup and the shoulder 114 of the plug first portion 108 abuts the outer rim region 22. The plug 102 seals an interior region of the cup or cavity 24 defined by the inner surface 14 of the cup and the top surface 126 of the plug. The stopcock 128 is set to an open position and the vacuum source 130 is activated to lower the pressure in the cavity 24 to a predetermined level. The pressure in the cavity 24 can range from about 0.0054 bar to about 1.013 bar. A preferred vacuum pressure is between about 0.8 bar and about 0.9 bar. After the cavity pressure reaches the desired level, the stopcock 128 is set to a closed position to maintain the vacuum in the cavity 24 and the hose 132 is then removed from the collar 120.

Figure 6:
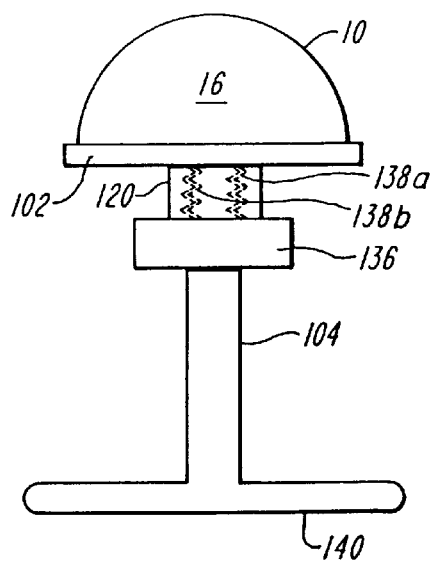
FIG. 6 is a block diagram showing the plug of FIG. 3 coupled to a handle.

As shown in FIG. 6, a distal end 136 of the handle or elongate member 104 is then secured to the plug at the collar 120. It is understood that the handle can be coupled to the collar 120 using a variety of mechanisms including threads, snap fit engagements, and set screws. In one embodiment, an inner surface of a bore formed in the collar 120 and the distal end 136 of the handle each have complementary threads 138a,b for threadable engagement of the handle and the plug.

Figure 7:
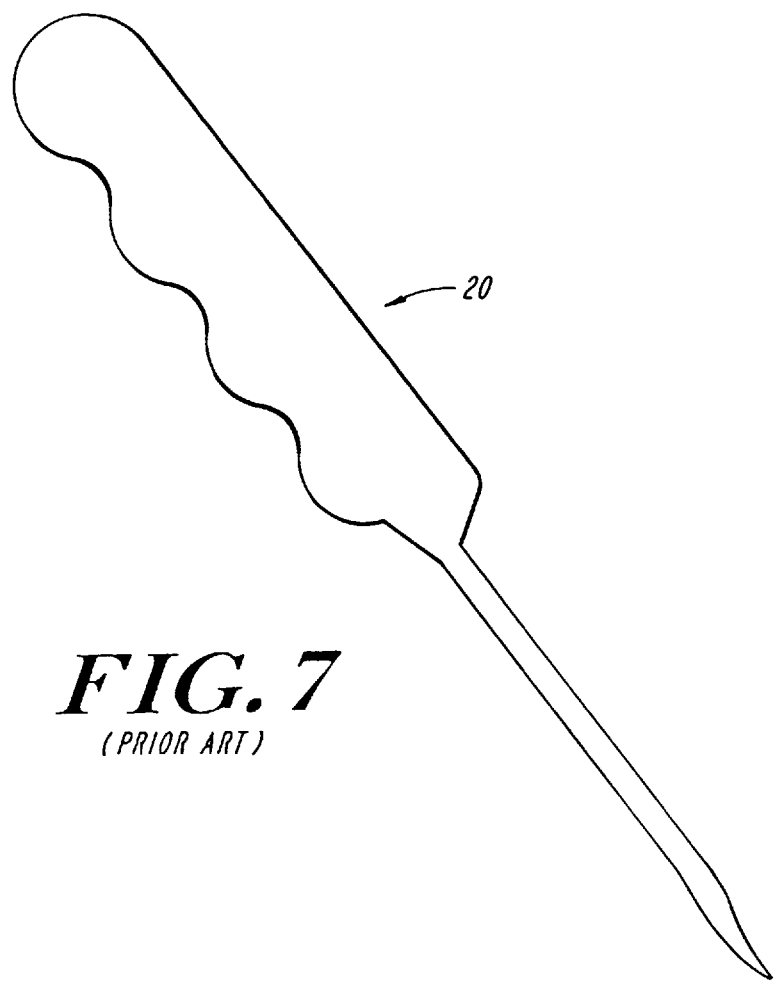
FIG. 7 is a perspective view of a prior art osteotome chisel useful in combination with an acetabular cup extraction system in accordance with the present invention.

The handle 104 facilitates the application of pressure to the acetabular cup 10 via the plug 102 for extracting the cup from the acetabulum. A proximal end 140 of the handle, which is readily graspable by a surgeon, is manipulable by a surgeon for gently rotating the implanted cup 10 to expose the cup outer surface. A conventional osteotome 20, such as that shown in FIG. 7, can be used to remove material, cement and bony ingrowth for example, which adheres the cup outer surface 16 to the acetabulum. As this material is removed, the cup 10 can be rotated through an increasingly greater angle so as to ultimately provide access to virtually the entire outer surface 16 of the cup. By advancing the osteotome 20 along the cup outer surface 16, the surgeon can extract the cup without removing excess, and possibly essential, bone and tissue.

Figure 8:
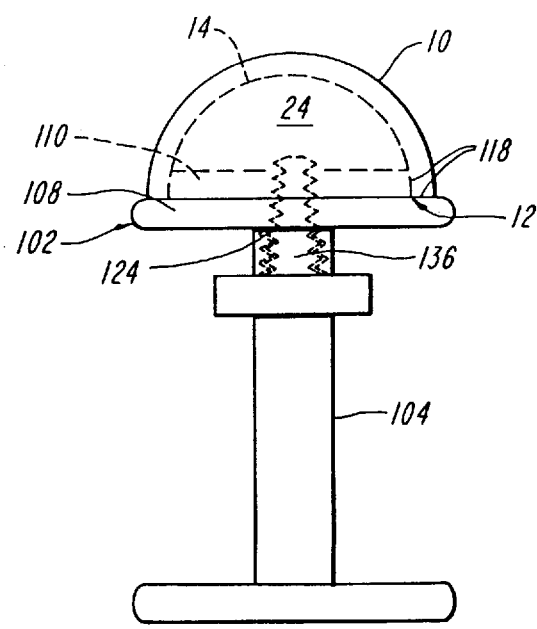
FIG. 8 is a front view of another embodiment of a cup extraction system in accordance with the present invention.

In another embodiment shown in FIG. 8, the threaded distal end 136 of the handle 104 is tapered. As the handle 104 is rotated for engagement with the corresponding passage 124 in the plug, the threaded distal end 136 applies pressure radially outward on the plug 102 so as to urge the mating surface 118 against the rim region 12 of the cup. It is understood that the passage 124 can have a taper corresponding to that of the handle distal end 136. With sufficient pressure, the sealed region 24 of the cup may not need to be evacuated. In one embodiment, the first end 136 of the handle forms a seal with the passage walls so as to allow evacuation of the cavity 24 via a separate passage (see FIG. 10).

Figure 9:
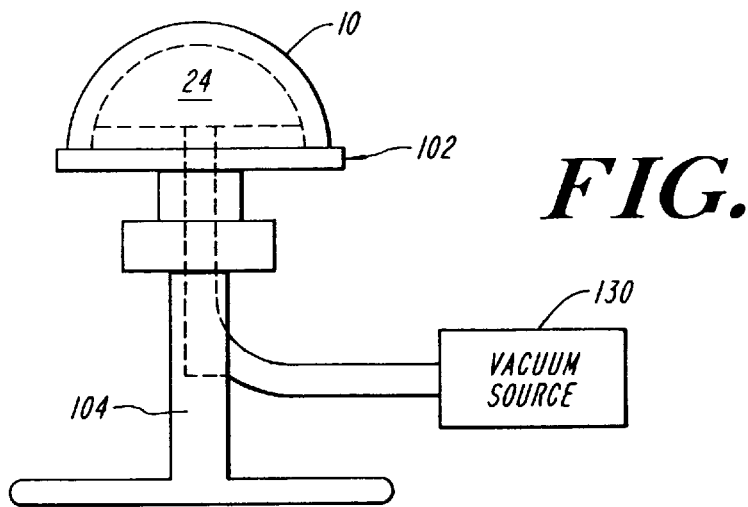
FIG. 9 is a front view of a further embodiment of a cup extraction system in accordance with the present invention.
Figure 10:
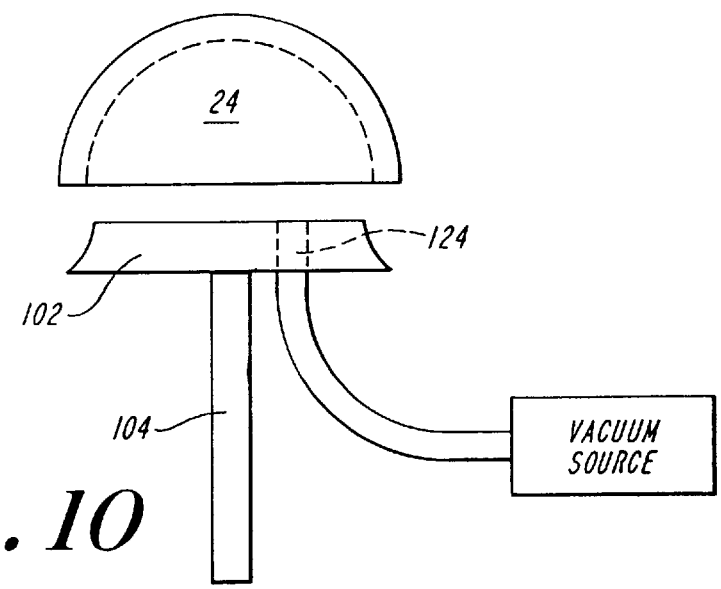
FIG. 10 is a front view of yet another embodiment of a cup extraction system in accordance with the present invention.

As shown in FIG. 9, the handle 104 may be hollow so as to provide a pathway for fluid communication between the vacuum source 130 and the interior region 24 of the cup. The distal end 136 of the handle can be threaded for sealed engagement with the corresponding passage 124, as shown in FIG. 8 for example. Alternatively, as shown in FIG. 10, the passage 124 formed in the plug can be spaced from the handle 104 to allow evacuation of the cup interior region 24.

Figure 11:
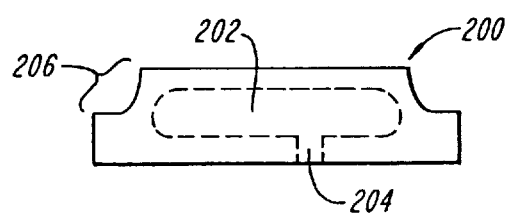
FIG. 11 is a front view of a plug which forms a portion of a cup extraction system in accordance with the present invention.

FIG. 11 shows another embodiment of a plug 200 for use in a cup extraction system in accordance with the present invention. The plug 200 has a chamber 202 formed therein into which a pressurized fluid can be placed, or which can be evacuated. A passage 204 connects the chamber 202 to the plug surface. It is understood that a handle can be secured to the plug for manipulation by a surgeon.

The chambered plug 200 can be used in a variety of techniques to achieve secure fixation of the plug to the cup 10 (FIGS. 1–2). In one embodiment, the plug 200 is seated within the rim region 12 of the cup and the chamber 202 is filled with a pressurized fluid. The mating surface 206 of the plug is thereby urged against the rim region 12 of the cup.

Alternatively, the chamber 202 is first evacuated to a predetermined pressure level and the plug 200 is mated with the cup 10. The vacuum in the chamber 202 is then released such that the mating surface 206 securely engages the cup rim.

Figure 12:
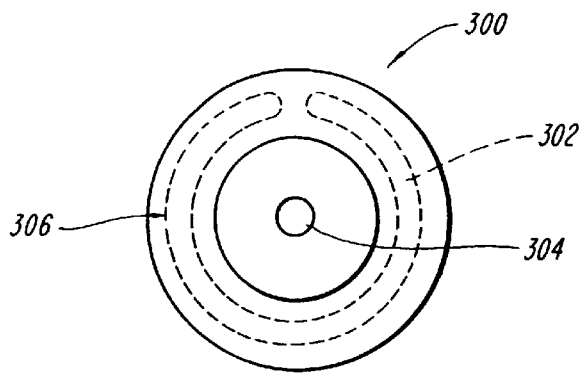
FIG. 12 is a top view of a plug which forms a portion of a cup extraction system in accordance with the present invention.

In another embodiment shown in FIG. 12, a plug 300 includes an annular member 302 disposed within an outer region of the plug. The annular member 302 is formed from a shape memory material, such as Nitinol, which has a thermally dependent geometry. That is, the annular member 302 has a first shape when at a first temperature and a second shape when at a second temperature. In one embodiment, the shape of the annular member 302 expands when it is heated.

In use, the plug 300 is seated within the cup rim and the annular member 302 is heated to a predetermined pressure which causes the overall geometry of the annular member to expand. The expansion of the annular member 302 pressures the mating surface of the plug against the cup rim.

Alternatively, the annular member 302 is cooled so as to decrease the overall geometry of the plug 300. The plug 300 is then mated with the acetabular cup 10 and the annular member 302 is heated such that the annular member geometry expands to secure the plug to the cup.

Figure 13:
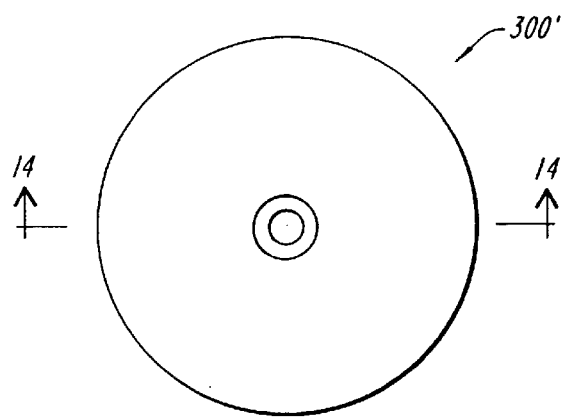
FIG. 13 is a top view of another embodiment of a plug which forms a portion of a cup extraction system in accordance with the present invention.
Figure 14:
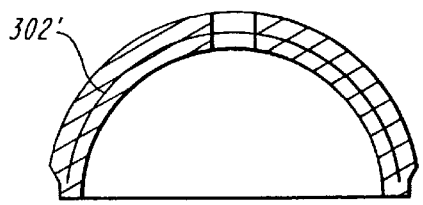
FIG. 14 is a cross-sectional view of the plug of FIG. 13 along line 14—14 with the plug shown in a first position.
Figure 15:
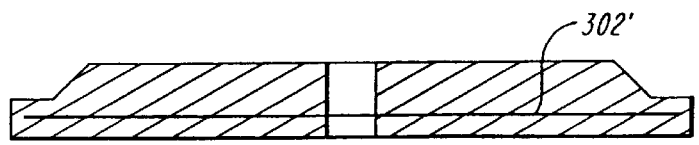
FIG. 15 is a cross-sectional view of the plug of FIG. 13 along line 14—14 with the plug shown in a second position.

FIGS. 13–15 show an alternative embodiment of a plug 300' having a disk 302' formed from a shape memory material, such as Nitinol, embedded within the plug. The disk 302 has a first shape, e.g., arcuate, which corresponds to a first temperature and a second shape, e.g., flat, which corresponds to a second temperature. In an exemplary embodiment, the disk 300' is activated, such as by heating, to transition the plug 300' from an initial concave shape (FIG. 14) to a generally flat shape (FIG. 15). In use, the plug 300' is seated within the rim of an acetabular cup and is then heated which causes the disk 302' to flatten and thereby apply radially outward pressure for engaging the plug within the cup rim.

Alternatively, the plug has a plurality of Nitinol wires embedded therein. Heating the initially curved wires causes them to flatten for pressuring the plug mating surface against the rim of the cup.

In a further embodiment, a plug is biased to a generally arcuate shape, like that shown in FIG. 14 for example, with a curvature opposite that of the cup outer surface. The plug can be formed from a semi-rigid, elastically deformable material. After the plug is seated within the rim region of the cup so as to form a seal, the interior region of the cup is evacuated. The vacuum causes the plug to flatten out such that a perimeter of the plug applies radially outward pressure on the inner rim region of the cup. The plug is thereby secured to the cup so as to facilitate the application of pressure to the cup via a handle coupled to the plug.

In general, the plug has a thickness that provides sufficient rigidity such that the plug resists displacement from the cup as pressure is applied to the attached handle. In an exemplary embodiment, the thickness ranges from about 1 millimeter to about 30 millimeters. It will be appreciated, however, that the geometry of the plug second portion 110 (FIG. 3) can substantially conform to that of the cup inner surface 14.

The plug can be formed from a variety of suitable materials such as rubber, silicone, polyurethane and polyethylene. Additional materials can be embedded within the plug including metals and plastics. It is understood that the mating surface of the plug can be formed from a further material for enhancing a seal between the plug and the cup. It is further understood that the plug can be reinforced using materials and techniques known to one of ordinary skill in the art.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A system for removing an implanted acetabular cup, comprising:
    a plug matable with a rim region of the acetabular cup having a generally annular shape and a recess formed about a circumference of the plug so as to define a mating surface which conforms to the rim region of the acetabular cup, the plug having a passage extending therethrough for connection with a vacuum source, a first surface and an opposite second surface on which a collar is disposed;
    a valve mechanism coupled to the passage: and an elongate member having a first end matable with the plug and a second end.

2. The system according to claim 1, wherein a cavity defined by an inner surface of the acetabular cup and the plug is evacuable by the vacuum source to a pressure ranging from about 0.0054 bar to about 1.0130 bar.

3. The system according to claim 1, wherein the plug has a thickness in the range from about 1 millimeter to about 30 millimeters.

4. The system according to claim 1, wherein the plug is substantially formed from a material selected from the group consisting of rubber, silicone, polyurethane, and polyethylene.

5. The system according to claim 1, wherein the passage extending through the plug is a centrally located bore having a threaded inner surface for engaging the first end of the elongate member.

6. The system according to claim 5, wherein the first end of the elongate member is tapered.

7. The system according to claim 6, wherein insertion of the first end of the elongate member into the bore urges the mating surface of the plug against the rim region of the acetabular cup so as to mechanically engage the elongate member and the acetabular cup.

8. The system according to claim 6, wherein the bore extends through the plug and is adapted for connection to a vacuum source.

9. The system according to claim 8, wherein the elongate member is hollow for allowing fluid communication through the elongate member between the vacuum source and an interior region of the cup.

10. The system according to claim 7, wherein a further bore extends through the plug for connection to a vacuum source.

11. The system according to claim 1, further including a fluid-impermeable member for being bonded to an apertured inner surface of the acetabular cup.

12. A system for removing an implanted acetabular cup, comprising:
    a plug matable with a rim region of the acetabular cup having a generally annular shape with a recess formed about a circumference of the plug so as to define a mating surface which is conformable to the rim region of the acetabular cup;
    an internal chamber formed within the plug that is in communication with a region external to the plug through a passageway; and
    an elongate member having a first end matable with the plug and a second end, wherein the plug has an outer surface that is selectively alterable between a first, arcuate shape and a second, substantially flat outer surface.

13. The system according to claim 12, wherein the internal chamber is adapted for receiving a pressurized fluid.

14. The system according to claim 12, wherein the internal chamber is adapted for being evacuated.

15. A acetabular cup extraction system, comprising:
    an annular, semi-rigid sealing member including a first disc-shaped portion having a first diameter and a second disc-shaped portion having a second diameter that is less than the first diameter, such that a circumferential portion of the sealing member forms a mating surface adapted for sealing engagement with a rim of an acetabular cup, the sealing member having a bore formed therethrough for evacuating an interior portion of the acetabular cup such that the mating surface of the semi-rigid sealing member is urged against the rim of the acetabular cup;
    a collar disposed on the first disc-shaped portion; and
    a handle having a distal end for releasable coupling to the collar and a proximal end for facilitating extraction of the implanted acetabular cup.

16. A system for removing an implanted acetabular cup, comprising:
    a plug matable with a rim region of the acetabular cup, the plug having a generally annular shape with a recess formed about a circumference of the plug so as to define a mating surface which is conformable to the rim region of the acetabular cup;
    at least member, formed of a shape memory material, embedded within the plug; and
    an elongate member having a first end matable with the plug and a second end.

* * * * *